US010634674B2

(12) United States Patent
Chung et al.

(10) Patent No.: US 10,634,674 B2
(45) Date of Patent: Apr. 28, 2020

(54) PROBE FOR DETECTING BACTERIA USING PEPTIDOGLYCAN-BINDING PROTEIN, AND USE THEREOF

(71) Applicant: Haesung Bio Co., Ltd., Daejeon (KR)

(72) Inventors: Bong Hyun Chung, Seoul (KR); Eun Kyung Lim, Daejeon (KR); Kyoung Sook Park, Daejeon (KR); Jong Min Choi, Daejeon (KR); Seong U. Kim, Seoul (KR); Heejun Lee, Seoul (KR)

(73) Assignee: Haesung Bio Co., Ltd., Daejeon (KR)

( * ) Notice: Subject to any disclaimer, the term of this patent is extended or adjusted under 35 U.S.C. 154(b) by 27 days.

(21) Appl. No.: 15/563,713

(22) PCT Filed: Apr. 7, 2016

(86) PCT No.: PCT/KR2016/003662
§ 371 (c)(1),
(2) Date: Nov. 28, 2017

(87) PCT Pub. No.: WO2016/163782
PCT Pub. Date: Oct. 13, 2016

(65) Prior Publication Data
US 2018/0080933 A1     Mar. 22, 2018

(30) Foreign Application Priority Data

Apr. 8, 2015 (KR) .................. 10-2015-0049601

(51) Int. Cl.
| | |
|---|---|
| *A61K 38/16* | (2006.01) |
| *C07K 1/00* | (2006.01) |
| *C07K 14/00* | (2006.01) |
| *C07K 17/00* | (2006.01) |
| *G01N 33/569* | (2006.01) |
| *C12N 1/20* | (2006.01) |
| *G01N 33/58* | (2006.01) |

(52) U.S. Cl.
CPC ........ *G01N 33/56911* (2013.01); *A61K 38/16* (2013.01); *C12N 1/20* (2013.01); *G01N 33/582* (2013.01); *C07K 14/00* (2013.01); *G01N 2400/00* (2013.01); *G01N 2400/10* (2013.01)

(58) Field of Classification Search
None
See application file for complete search history.

(56) References Cited

U.S. PATENT DOCUMENTS

| | | | |
|---|---|---|---|
| 4,970,152 A | 11/1990 | Ashida et al. | |
| 5,747,277 A | 5/1998 | Tsuchiya | |
| 2005/0222326 A1* | 10/2005 | Kulkarni | ............... C08F 220/36 525/54.2 |
| 2012/0244595 A1* | 9/2012 | Loessner | .................. C12N 9/14 435/188 |

FOREIGN PATENT DOCUMENTS

WO    WO 2013/033436 A1    3/2013

OTHER PUBLICATIONS

Dziarski, Molec. Immunol. 40:877-886 (2004) (Year: 2004).*
UniProt Accession No. Q96LB9, 12 pages (2001) (Year: 2001).*
Liu et al., J. Biol. Chem. 276:34686-34694 (2001) (Year: 2001).*
Chen et al., Adv. Drug Deliv. Rev. 65:1357-1369 (2013) (Year: 2013).*
Hayward et al., J. Biol. 9:12 (2010) (Year: 2010).*
ThermoFisher Scientific, "Long-Wavelength Rhodamines, Texas Red Dyes and QSY Quenchers-Section 1.6," available online (See web link in Action), 15 pages (first available Dec. 2015) (Year: 2015).*
Merriam-Webster, "Definition of complex", available online at https://www.merriam-webster.com/dictionary/complex, 15 pages (accessed on Sep. 3, 2019) (Year: 2019).*
Chemicool.com, "Definition of Compound", available online at https://www.chemicool.com/definition/compound.html, 2 pages (first available 2017) (Year: 2017).*
Vollmer et al., FEMS Microbiol. Rev. 32:149-167 (2008) (Year: 2008).*
Lugtenberg et al., Antimicrob. Agents Chemother. 2:485-491 (1972) (Year: 1972).*
Merriam-Webster, "Bound," available online at https://www.merriam-webster.com/dictionary/bound, 13 pages (accessed on Sep. 10, 2019) (Year: 2019).*
Helmenstine, "What Is a Covalent Bond in Chemistry", available online at https://www.thoughtco.com/definition-of-covalent-bond-604414, 9 pages (2019) (Year: 2019).*
Charroux, B., et al., "Bacterial Detection by *Drosophila peptidoglycan* Recognition Proteins" *Microbes and Infection*, 2009, 11: 631-636.
Dancer, S.J., "How antibiotics can make us sick: the less obvious adverse effects of antimicrobial chemotherapy", *The Lancet, Infectious Disease*, vol. 4, Oct. 2004, pp. 611-619.

(Continued)

*Primary Examiner* — James H Alstrum-Acevedo
*Assistant Examiner* — Thea D'Ambrosio
(74) *Attorney, Agent, or Firm* — Hamilton, Brooks, Smith & Reynolds, P.C.

(57) ABSTRACT

The present invention relates to a probe for detecting bacteria using a peptidoglycan-binding protein, and a method for preparing the same. Also, the present invention relates to a method for detecting bacteria using the probe.
The probe for detecting bacteria according to the present invention can specifically detect bacteria. That is, the probe according to the present invention can clearly distinguish between yeast and bacteria and can detect both Gram-negative and Gram-positive bacteria, and thus is expected to be usable in various fields as a universal probe for detecting bacteria. Further, use of the probe allows bacteria to be detected by identifying only fluorescence development without an additional enzymatic treatment, thereby enabling a simple and quick bacterial detection. In particular, the probe is expected to be effectively usable in the food industry where quick bacterial detection is required.

7 Claims, 6 Drawing Sheets

Specification includes a Sequence Listing.

(56) References Cited

OTHER PUBLICATIONS

English translation of the Written Opinion for International Application No. PCT/KR2016/003662, "Systems and Methods for Mobile Device Analysis of Nucleic Acids and Proteins", 2 pgs., dated Aug. 12, 2016.
International Search Report of International Application No. PCT/KR2016/003662, "Systems and Methods for Mobile Device Analysis of Nucleic Acids and Proteins", 2 pgs., dated Aug. 12, 2016.
NCBI, GenBank accession No. AAI28116.1 (Dec. 5, 2006).
NCBI, GenBank accession No. EAW53338 (Mar. 23, 2015).
Ogawa, M., et al., "Fluorophore-Quencher based Activatable Targeted Optical Probes for Detecting in Vivo Cancer Metastases", *Molecular Pharmaceutics*, 2009, 6(2): 386-395.
Sauvage, E., et al., "The Penicillin-binding Proteins: Structure and Role in Peptidoglycan Biosynthesis", FEMS Microbiology Reviews, 2008, 32: 234-258.

\* cited by examiner

SEQUENCE LISTING

<160> NUMBER OF SEQ ID NOS: 3

<210> SEQ ID NO 1
<211> LENGTH: 166

```
<212> TYPE: PRT
<213> ORGANISM: Artificial Sequence
<220> FEATURE:
<223> OTHER INFORMATION: PGBP

<400> SEQUENCE: 1

Met Val Cys Pro Asn Ile Ile Lys Arg Ser Ala Trp Glu Ala Arg Glu
1               5                   10                  15

Thr His Cys Pro Lys Met Asn Leu Pro Ala Lys Tyr Val Ile Ile Ile
            20                  25                  30

His Thr Ala Gly Thr Ser Cys Thr Val Ser Thr Asp Cys Gln Thr Val
        35                  40                  45

Val Arg Asn Ile Gln Ser Phe His Met Asp Thr Arg Asn Phe Cys Asp
50                  55                  60

Ile Gly Tyr His Phe Leu Val Gly Gln Asp Gly Val Tyr Glu Gly
65                  70                  75                  80

Val Gly Trp His Ile Gln Gly Ser His Thr Tyr Gly Phe Asn Asp Ile
                85                  90                  95

Ala Leu Gly Ile Ala Phe Ile Gly Tyr Phe Val Glu Lys Pro Pro Asn
            100                 105                 110

Ala Ala Ala Leu Glu Ala Ala Gln Asp Leu Ile Gln Cys Ala Val Val
        115                 120                 125

Glu Gly Tyr Leu Thr Pro Asn Tyr Leu Leu Met Gly His Ser Asp Val
130                 135                 140

Val Asn Ile Leu Ser Pro Gly Gln Ala Leu Tyr Asn Ile Ile Ser Thr
145                 150                 155                 160

Trp Pro His Phe Lys His
            165

<210> SEQ ID NO 2
<211> LENGTH: 421
<212> TYPE: PRT
<213> ORGANISM: Artificial Sequence
<220> FEATURE:
<223> OTHER INFORMATION: eGFP-PGBP-1a

<400> SEQUENCE: 2

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Phe Ile
        35                  40                  45

Cys Thr Thr Gly Lys Leu Pro Val Pro Trp Pro Thr Leu Val Thr Thr
50                  55                  60

Leu Thr Tyr Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160
```

Gly Ile Lys Val Asn Phe Lys Ile Arg His Asn Ile Glu Asp Gly Ser
            165                 170                 175

Val Gln Leu Ala Asp His Tyr Gln Gln Asn Thr Pro Ile Gly Asp Gly
        180                 185                 190

Pro Val Leu Leu Pro Asp Asn His Tyr Leu Ser Thr Gln Ser Ala Leu
    195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys Gly
225                 230                 235                 240

Gly Ser Gly Ser Gly Glu Phe Met Val Cys Pro Asn Ile Ile Lys Arg
            245                 250                 255

Ser Ala Trp Glu Ala Arg Glu Thr His Cys Pro Lys Met Asn Leu Pro
        260                 265                 270

Ala Lys Tyr Val Ile Ile His Thr Ala Gly Thr Ser Cys Thr Val
    275                 280                 285

Ser Thr Asp Cys Gln Thr Val Val Arg Asn Ile Gln Ser Phe His Met
290                 295                 300

Asp Thr Arg Asn Phe Cys Asp Ile Gly Tyr His Phe Leu Val Gly Gln
305                 310                 315                 320

Asp Gly Gly Val Tyr Glu Gly Val Gly Trp His Ile Gln Gly Ser His
            325                 330                 335

Thr Tyr Gly Phe Asn Asp Ile Ala Leu Gly Ile Ala Phe Ile Gly Tyr
        340                 345                 350

Phe Val Glu Lys Pro Pro Asn Ala Ala Leu Glu Ala Gln Asp
    355                 360                 365

Leu Ile Gln Cys Ala Val Val Glu Gly Tyr Leu Thr Pro Asn Tyr Leu
370                 375                 380

Leu Met Gly His Ser Asp Val Val Asn Ile Leu Ser Pro Gly Gln Ala
385                 390                 395                 400

Leu Tyr Asn Ile Ile Ser Thr Trp Pro His Phe Lys His Leu Glu His
            405                 410                 415

His His His His His
        420

<210> SEQ ID NO 3
<211> LENGTH: 421
<212> TYPE: PRT
<213> ORGANISM: Artificial Sequence
<220> FEATURE:
<223> OTHER INFORMATION: PGBP-1a-eGFP

<400> SEQUENCE: 3

Met Val Cys Pro Asn Ile Ile Lys Arg Ser Ala Trp Glu Ala Arg Glu
1               5                   10                  15

Thr His Cys Pro Lys Met Asn Leu Pro Ala Lys Tyr Val Ile Ile
        20                  25                  30

His Thr Ala Gly Thr Ser Cys Thr Val Ser Thr Asp Cys Gln Thr Val
            35                  40                  45

Val Arg Asn Ile Gln Ser Phe His Met Asp Thr Arg Asn Phe Cys Asp
    50                  55                  60

Ile Gly Tyr His Phe Leu Val Gly Gln Asp Gly Val Tyr Glu Gly
65                  70                  75                  80

Val Gly Trp His Ile Gln Gly Ser His Thr Tyr Gly Phe Asn Asp Ile
                85                  90                  95

```
Ala Leu Gly Ile Ala Phe Ile Gly Tyr Phe Val Glu Lys Pro Pro Asn
            100                 105                 110

Ala Ala Ala Leu Glu Ala Ala Gln Asp Leu Ile Gln Cys Ala Val Val
            115                 120                 125

Glu Gly Tyr Leu Thr Pro Asn Tyr Leu Leu Met Gly His Ser Asp Val
            130                 135                 140

Val Asn Ile Leu Ser Pro Gly Gln Ala Leu Tyr Asn Ile Ile Ser Thr
145                 150                 155                 160

Trp Pro His Phe Lys His Glu Phe Gly Gly Ser Gly Ser Gly Met Val
                165                 170                 175

Ser Lys Gly Glu Glu Leu Phe Thr Gly Val Val Pro Ile Leu Val Glu
            180                 185                 190

Leu Asp Gly Asp Val Asn Gly His Lys Phe Ser Val Ser Gly Glu Gly
            195                 200                 205

Glu Gly Asp Ala Thr Tyr Gly Lys Leu Thr Leu Lys Phe Ile Cys Thr
            210                 215                 220

Thr Gly Lys Leu Pro Val Pro Trp Pro Thr Leu Val Thr Thr Leu Thr
225                 230                 235                 240

Tyr Gly Val Gln Cys Phe Ser Arg Tyr Pro Asp His Met Lys Gln His
                245                 250                 255

Asp Phe Phe Lys Ser Ala Met Pro Glu Gly Tyr Val Gln Glu Arg Thr
            260                 265                 270

Ile Phe Phe Lys Asp Asp Gly Asn Tyr Lys Thr Arg Ala Glu Val Lys
            275                 280                 285

Phe Glu Gly Asp Thr Leu Val Asn Arg Ile Glu Leu Lys Gly Ile Asp
            290                 295                 300

Phe Lys Glu Asp Gly Asn Ile Leu Gly His Lys Leu Glu Tyr Asn Tyr
305                 310                 315                 320

Asn Ser His Asn Val Tyr Ile Met Ala Asp Lys Gln Lys Asn Gly Ile
                325                 330                 335

Lys Val Asn Phe Lys Ile Arg His Asn Ile Glu Asp Gly Ser Val Gln
            340                 345                 350

Leu Ala Asp His Tyr Gln Gln Asn Thr Pro Ile Gly Asp Gly Pro Val
            355                 360                 365

Leu Leu Pro Asp Asn His Tyr Leu Ser Thr Gln Ser Ala Leu Ser Lys
            370                 375                 380

Asp Pro Asn Glu Lys Arg Asp His Met Val Leu Leu Glu Phe Val Thr
385                 390                 395                 400

Ala Ala Gly Ile Thr Leu Gly Met Asp Glu Leu Tyr Lys Leu Glu His
                405                 410                 415

His His His His
        420
```

PROBE FOR DETECTING BACTERIA USING PEPTIDOGLYCAN-BINDING PROTEIN, AND USE THEREOF

This application is the U.S. National Stage of International Application No. PCT/KR2016/003662, filed Apr. 7, 2016, which designates the U.S., published in Korean, and claims priority under 35 U.S.C. §§ 119 or 365(c) to Korean Application No. 10-2015-0049601, filed Apr. 8, 2015. The entire teachings of the above applications are incorporated herein by reference.

INCORPORATION BY REFERENCE OF MATERIAL IN ASCII TEXT FILE

This application incorporates by reference the Sequence Listing contained in the following ASCII text file:
 a) File name: 55021001001_SEQUENCE_LISTING_UPDATED; created Jan. 17, 2020, 10 KB in size.

TECHNICAL FIELD

The present invention relates to a probe for detecting bacteria using a peptidoglycan-binding protein.

In addition, the present invention relates to a method for preparing the probe for detecting bacteria using a peptidoglycan-binding protein.

Further, the present invention relates to a method for detecting bacteria using the probe.

BACKGROUND ART

In daily lives, people are unwittingly exposed to surfaces contaminated with microorganisms that may cause diseases. Many studies have shown that "dangerous spots" contaminated with certain bacteria involve cross-contamination from public telephones, door handles, hospital waiting rooms and toys in day-care centers for children, hot air hand dryers, towels and sponges used in kitchens, hands of hospital staff doing routine patient care, and surfaces of kitchen counters and knives where raw meat and vegetables are mingled.

In South Korea, the occurrence of bacterial contamination in various regions has resulted in the death of children and the elderly and has caused many people to become ill. In addition, microbial contamination of food is a major problem all around the world. *Salmonella, E. coli,* and other food-derived bacteria are causing an uncountable number of diseases every year. Acute symptoms include nausea, vomiting, abnormal abdominal pain, diarrhea, high fever, and headache. The onset of acute symptoms is followed by chronic consequences. It may be a great help if the presence of bacteria on surfaces of kitchen counters is simply detectable, since cross-contamination may cause bacteria derived from meat, fish, and poultry to be transferred to non-cooked foods such as vegetables.

Likewise, detecting the hazardous level of microorganisms in the food processing industry is very important in maintaining home and consumer health. Thus, monitoring of bacteria is important in the food processing industry. Processing of virtually all food products, from meat packaging to cheese production, involves monitoring microbial levels to ensure the safety in supplying food products.

In particular, beer contains not only alcohol, bittern components, and carbon dioxide but also has low pH and very low oxygen concentration, thereby not providing an environment suitable for microorganisms to inhabit. However, even in these unsuitable environmental conditions, some microorganisms are detected in beer. These microorganisms are classified as harmful beer microorganisms. Such harmful beer microorganisms not only cause beer haze but also cause beer spoilage and further cause various diseases due to bacterial contamination.

The harmful consequences caused by microbial contamination are not limited to the food industry. In recent decades, there has been a drastic increase in the number of "superbugs" and it is problematic that hospitals and health communities are sources for the superbugs. Abuse of antibiotics as well as insufficient cleanliness in hospitals has brought about vancomycin-resistant *enterococci* and other Gram-negative bacilli, in addition to methicillin-resistant *S. aureus* (MRSA), and *Clostridium difficile* (Dancer, 2004). According to a recent BBC's report, the death toll due to MRSA is estimated to be 5,000 people per year. The article has shown that "cleanliness is a major concern that patients have and the MRSA problem is becoming more serious.". Considering that many patients in hospitals are already immune-deficient and thus are at greater risk of being infected, risks due to malignant bacteria in a hospital environment become even more threatening.

Bacteria existing in trace amounts in various types of specimens may be identified by detecting and measuring a peptidoglycan which is a cell wall component of bacteria. A peptidoglycan is a glycoprotein polymer containing N-acetylmuramic acid or N-glycosylmuramic acid and D-amino acid, which is a component of bacterial cell walls and forms a thin layer inside outer membranes of cell walls. Therefore, detecting and measuring a peptidoglycan may be applied to stability tests for pharmaceuticals, tests for microorganisms in water and food products, and diagnosis of infectious diseases.

As an example of compositions and methods for detecting a peptidoglycan, U.S. Pat. No. 4,970,152 discloses a composition for specifically detecting a peptidoglycan by removing proteins that react with beta-1,3-glucan from a plasma fluid of silkworm larvae. However, the composition requires the addition of calcium ions to cause phenol oxidase activity to be exerted by a peptidoglycan. That is, according to U.S. Pat. No. 4,970,152, when a body fluid is collected from an insect, it is required to add calcium ions so that activation of phenol oxidase is inhibited by calcium ions to obtain a phenol oxidase composition and the composition is used to cause color development using a peptidoglycan as a substrate.

In addition, U.S. Pat. No. 5,747,277 discloses an SLP reagent, but it does not specifically react with only a peptidoglycan because it detects a beta-1,3-glucan and a peptidoglycan at the same time.

Therefore, it is urgently needed to develop a detection system capable of quickly identifying the presence of bacteria through reaction with a peptidoglycan, for quick detection and diagnosis of bacteria which may cause diseases.

DISCLOSURE

Technical Problem

For this purpose, the present inventors have made intensive efforts to develop an effective bacterial detection system that specifically binds to a peptidoglycan of bacteria to generate fluorescence signals, thereby completing a probe for detecting bacteria of the present invention.

Accordingly, an object of the present invention is to provide a probe for detecting bacteria using a peptidoglycan-binding protein.

Another object of the present invention is to provide a method for preparing the probe for detecting bacteria using a peptidoglycan-binding protein.

A further object of the present invention is to provide a method for detecting bacteria using the probe.

Technical Solution

In order to achieve the above objects, the present invention provides a probe for detecting bacteria, including a peptidoglycan-binding protein (PGBP), a fluorescent material and a quencher.

The present invention will be described in detail below.

In the present invention, "peptidoglycan-binding protein" is a protein containing a peptidoglycan-binding domain capable of binding to a peptidoglycan, and the type thereof is not limited. In a specific embodiment of the present invention, a probe was constructed using a peptidoglycan-binding protein consisting of the amino acid sequence of SEQ ID NO: 1.

In the present invention, the fluorescent material is a substance that generates fluorescence when it is physically distanced from the quencher, and the type thereof is not limited. Examples of the fluorescent material include a luminous molecule, a metal ion, a complex compound, an organic dye, a conductor, a semiconductor, an insulator, a quantum dot, a quantum wire, and the like which emit light at their excited state.

Examples of the fluorescent material include fluorescent proteins such as enhanced green fluorescent protein (EGFP), enhanced cyan fluorescent protein (ECFP), enhanced blue fluorescent protein (EBFP), enhanced yellow fluorescent protein (EYFP), and red fluorescent protein (RFP).

Also, examples of the fluorescent material may include Pyrene or its derivatives, Cyanine (Cy) series, Alexa Fluor series, BODIPY series, DY series, rhodamine or its derivatives, Fluorescein or its derivatives, coumarin or its derivatives, Acridine homodimer or its derivatives, Acridine orange or its derivatives, 7-aminoactinomycin D (7-AAD) or its derivatives, Actinomycin D or its derivatives, 9-amino-6-chloro-2-methoxyacridine (ACMA) or its derivatives, DAPI or its derivatives, Dihydroethidium or its derivatives, Ethidium bromide or its derivatives, Ethidium homodimer-1 (EthD-1) or its derivatives, Ethidium homodimer-2 (EthD-2) or its derivatives, Ethidium monoazide or its derivatives, Hexidium iodide or its derivatives, bisbenzimide (Hoechst 33258) or its derivatives, Hoechst 33342 or its derivatives, Hoechst 34580 or its derivatives, hydroxystilbamidine or its derivatives, LDS 751 or its derivatives, Propidium iodide (PI) or its derivatives, Calcein or its derivatives, Oregon Green or its derivatives, Magnesium Green or its derivatives, Calcium Green or its derivatives, JOE or its derivatives, tetramethylrhodamine or its derivatives, TRITC or its derivatives, N,N,N',N'-tetramethyl-6-carboxyrhodamine (TAMRA) or its derivatives, Pyronin Y or its derivatives, Lissamine or its derivatives, ROX or its derivatives, Calcium Crimson or its derivatives, Texas Red or its derivatives, Nile Red or its derivatives, Thiadicarbocyanine or its derivatives, dansylamide or its derivatives, cascade blue, 4',6-diamidino-2-phenylindole (DAPI).

A quantum dot may be used as the fluorescent material. The quantum dot is particle, which is formed largely of nano-sized II-IV or III-V semiconductor particles, and consists of a core of about 2 to 10 nm in size and a shell mainly composed of ZnS, etc. Even if the same material is used, fluorescence wavelength may vary depending on the particle size, and thus a various range of wavelength may be obtained. The Group II-VI or Group III-V compounds forming the quantum dot may be selected from the group consisting of CdSe, CdSe/ZnS, CdTe/CdS, CdTe/CdTe, ZnSe/ZnS, ZnTe/ZnSe, PbSe, PbS InAs, InP, InGaP, InGaP/ZnS and HgTe, and may be in the form of a single core or a core/shell.

In an embodiment of the present invention, TARMA was used as the fluorescent material.

As used herein, the term "quencher" includes a light extinguisher, a light absorber or the like, meaning a substance that absorbs energy or light from a fluorescent material or a light source. The quencher may be a light absorbing protein, a light absorbing molecule, a metal nano-particle, a carbon particle, or the like. Preferably, the quencher may be any one selected from the group consisting of Black Hole Quencher-1 (BHQ-1), DABCYL, Eclipse, TAMRA, QSY-7, Black Hole Quencher-2 (BHQ-2), and Black Hole Quencher-3 (BHQ-3), and the type thereof is not limited as long as it can absorb energy or light emitted from the labeling substance. In an embodiment of the present invention, BHQ-2 was used. The quencher is bound to N-acetylmuramic acid (NAA) or N-acetyl-D-glucosamine (NAG) and may be linked to a peptidoglycan through N-acetylmuramic acid or N-acetyl-D-glucosamine. In this case, the ratio of a peptidoglycan-binding protein to a quencher in the probe may be 1:1 to 40 (v/v), preferably 1:5 to 20 (v/v), but is not limited thereto.

The type of bacteria which is detectable by the probe according to the present invention is not limited. Specifically, the bacteria may be a Gram-negative bacteria or a Gram-positive bacteria. Examples of the Gram-negative bacteria include *Escherichia coli* (*E. coli*), *Helicobacter, Hemophilus, Neisseria, Cyano bacteria, Thiobacter, Borrelia, Burkholderia, Serratia, Treponema*, and the like. Examples of the Gram-positive bacteria include *Bacillus, Nocardia, Clostridium, Propionibacterium, Actinomyces, Enterococcus, Corynebacterium, Listeria, Lactobacillus, Gardnerella, Mycobacterium, Mycoplasma, Staphylococcus, Streptomyces, Streptococcus*, and the like, and all bacteria having a peptidoglycan may be included.

The operation principle of the probe according to the present invention is illustrated in FIG. 1. Also, the location of a peptidoglycan layer in bacteria and the operation principle of the probe according to the present invention are also illustrated in FIG. 6.

In addition, the present invention provides a method for preparing a probe for detecting bacteria, in which the method includes the steps of: (S1) binding a fluorescent molecule to a peptidoglycan-binding protein; (S2) preparing a quencher to which N-acetylmuramic acid or N-acetyl-D-glucosamine is bound; and (S3) binding the fluorescent molecule-bound peptidoglycan-binding protein in S1, with the quencher to which N-acetylmuramic acid or N-acetyl-D-glucosamine is bound in S2.

The above steps will be described in detail as follows. However, the following method is given to illustrate the present invention, and the scope of the present invention is not limited to the following description.

The step (S1) is a step of preparing a fluorescent molecule-bound peptidoglycan-binding protein. This step may include steps of (S1-1) dispersing and mixing Nα,Nα-bis (carboxymethyl)-L-lysine hydrate and TAMRA-NHS in a buffer; (S1-2) mixing nickel chloride with the reactant resulting from (S1-1); (S1-3) mixing a peptidoglycan-binding protein with the reactant resulting from (S1-2); and (S1-4) purifying the TAMRA-bound peptidoglycan-binding protein.

The mixing in (S1-1) may be performed for 12 to 48 hours. The mixing in (S1-2) may be performed for 30 minutes to 2 hours. The mixing in (S1-3) may be performed for 12 to 48 hours.

In addition, the step (S2) is a step of preparing a quencher to which N-acetylmuramic acid or N-acetyl-D-glucosamine is bound. This step may include steps of (S2-1) dispersing and mixing N-acetylmuramic acid or N-acetyl-D-glucosamine, EDC and sulfo-NHS in a buffer; and (S2-2) mixing and reacting BHQ2-amine with the reactant resulting from (S2-1). The mixing in (S2-1) may be performed for 6 to 24 hours. The reaction in (S2-2) may be performed for 6 to 48 hours.

Further, the step (S3) is a step of interconnecting the fluorescent molecule-bound peptidoglycan-binding protein with the quencher to which N-acetylmuramic acid or N-acetyl-D-glucosamine is bound.

The step (S3) may include the steps of (S3-1) binding the reactant resulting from S1 with the reactant resulting from S2; and (S3-2) purifying the reactant resulting from (S3-1). The binding in (S3-1) may be performed for 12 to 48 hours.

The probe for detecting bacteria according to the present invention can specifically detect bacteria. That is, the probe according to the present invention can clearly distinguish between yeast and bacteria and can detect both Gram-negative and Gram-positive bacteria, and thus is expected to be usable in various fields as a universal probe for detecting bacteria. Further, the probe allows bacteria to be detected by identifying only fluorescence development without an additional enzymatic treatment, thereby enabling a simple and quick bacterial detection. In particular, the probe is expected to be effectively usable in the food industry where quick bacterial detection is required.

Accordingly, the present invention provides a method for detecting bacteria using the probe.

In other words, the present invention provides a method for detecting bacteria, in which the method includes the step of treating a sample with the probe.

The type of the sample is not limited. The sample is a composition which contains or is suspected of containing microorganisms, and thus an analysis may be performed for, and may include a sample collected from any one or more of liquid, soil, air, food products, waste, animal/plant organs, and animal/plant tissues. In this case, the liquid may be characterized by beverage, liquor, water, blood, urine, tears, sweat, saliva, lymphatic and cerebrospinal fluids, and the like; the water includes river water, sea water, lake water, and rain water; the waste includes sewage, wastewater, and the like; and the animal/plant includes a human body. The animal/plant tissues may include tissues such as mucous membrane, skin, envelope, hair, scales, eyeball, tongue, cheek, hoof, beak, snout, foot, hand, mouth, nipple, ear, nose, and the like.

The probe according to the present invention is characterized in that the fluorescence development from a fluorescent material is inhibited by a quencher before binding to a peptidoglycan of bacteria, and fluorescence is developed by binding to the peptidoglycan of bacteria.

Advantageous Effects

The probe for detecting bacteria according to the present invention can specifically detect bacteria. That is, the probe according to the present invention can clearly distinguish between yeast and bacteria and can detect both Gram-negative and Gram-positive bacteria, and thus is expected to be usable in various fields as a universal probe for detecting bacteria. Further, the probe allows bacteria to be detected by identifying only fluorescence development without an additional enzymatic treatment, thereby enabling a simple and quick bacterial detection. In particular, the probe is expected to be effectively usable in the food industry where quick bacterial detection is required.

MODES OF THE INVENTION

Figure 1:
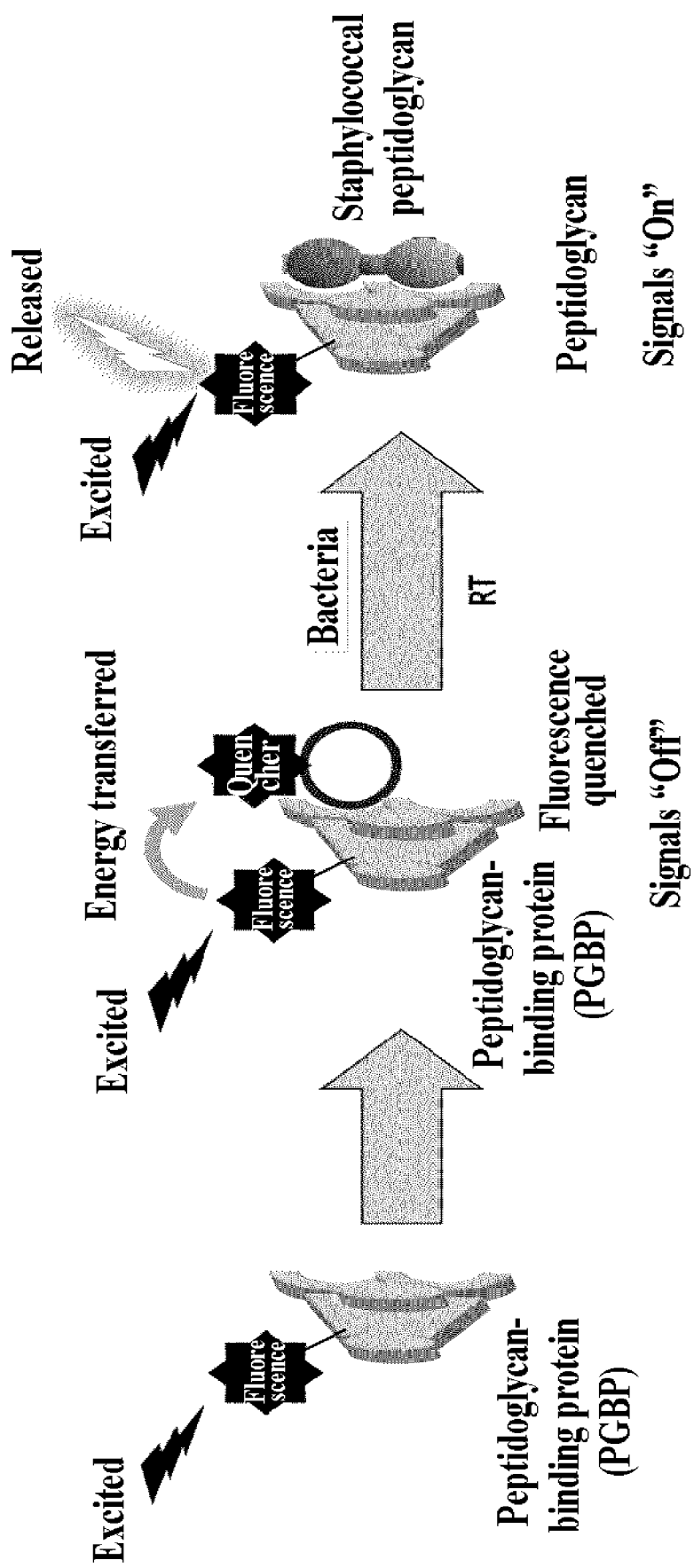
FIG. 1 illustrates a view of illustrating the operation principle of the probe for detecting bacteria according to the present invention.

The present invention will be described in more detail below with reference to examples. However, these examples are given to illustrate the present invention, and the scope of the present invention is not limited to these examples.

Example 1. Expression and Purification of Protein for Detecting Bacteria

The expression vector pET21a-eGFP-PGBP-1a (GP) or pET21a-PGBP-1a-eGFP (PG) was constructed so that a peptidoglycan-binding protein (PGBP) and eGFP are expressed as a fusion protein. Each of the constructed expression vectors was transduced into a recombinant protein-expressing *Escherichia coli*, *E. coli* BL21 (DE3), then the obtained transformant was inoculated into LB liquid medium supplemented with 50 μl/ml of ampicillin and cultured at 37° C. to 0.6 OD, then IPTG at a concentration of 1 mM was added, followed by shaking culture for 4 more hours to express the recombinant protein eGFP-PGBP-1a (SEQ ID NO: 2) (GP) or PGBP-1a-eGFP (SEQ ID NO: 3) (PG) for detecting bacteria.

In order to extract the expressed recombinant protein, 20 mM Tris-Cl (pH 8.0) and 0.2 M NaCl buffer solution were added to the *E. coli* cells recovered by centrifugation to thereby suspend the cells, and the cells were disrupted with an ultrasonic homogenizer. For efficient refolding of the protein produced as insoluble, it was first dissolved in 8M urea solution, and then metal affinity chromatography was performed using 6 histidines as a metal affinity tag. In order to convert the purified inactive recombinant protein into an active form, stirring was performed for 48 hours in a cold room (4° C.) in a refolding solution of 50 mM Tris-HCl (pH 8.5) containing 1 M arginine, 2 mM EDTA, 5 mM cysteamine, and 0.5 mM cystamine using a dialysis membrane with a concentration gradient of 0 to 500 mM imidazole. After sufficient refolding process, the buffer was exchanged to final PBS (pH 7.4), and then the recombinant protein was concentrated to 1 mg/ml using ultrafiltration (molecular cut off: 10 kDa).

Example 2. Preparation of Probe for Detecting Bacteria

The following steps were performed to prepare the probe for detecting bacteria of the present invention.

Step 1 (TAMRA-PG or TAMRA-GP): In order to bind a fluorescent molecule to the recombinant protein obtained in Example 1, Nα,Nα-bis (carboxymethyl)-L-lysine hydrate (5 mg) was first dispersed in phosphate buffered saline (PBS) (5 ml) and TAMRA-NHS (6.7 mg) was dispersed and mixed for 24 hours. Then, nickel chloride (9.6 mg) was added to the reactant, followed by mixing for 1 hour. Then, the recombinant protein, PG or GP (10 µl, 0.5 mg/ml) was added and mixed for 24 hours. Subsequently, an excess of reactants was removed using Centricon (MWCO: 10000 Da).

Step 2-1 (Quencher-NAA): N-acetylmuramic acid (NAA) (3 mg), EDC (2.4 mg), and sulfo-NHS (1.4 mg) were dispersed in MES buffer (2 ml) and then mixed. Then, BHQ2-amine (5.8 mg) was added and mixed for 12 hours or more.

Step 2-2 (Quencher-NAG): N-acetyl-D-glucosamine (NAG) (2.5 mg) was dispersed in DMF (10 ml) and then mixed with CDI (5.5 mg). Then, BHQ2-amine (6.5 mg) was added and mixed for 12 hours or more.

Step 3: TAMRA-GP or TAMRA-PG produced in Step 1 was bound with Quencher-NAA in Step 2-1 or Quencher-NAG in Step 2-2, respectively, to prepare TAMRA-GP: Quencher-NAA, TAMRA-GP: Quencher-NAG, TAMRA-PG: Quencher-NAA, and TAMRA-GP: Quencher-NAG. After preparation, unbound reactants were removed using Centricon (MWCO: 10000 Da).

Figure 2:
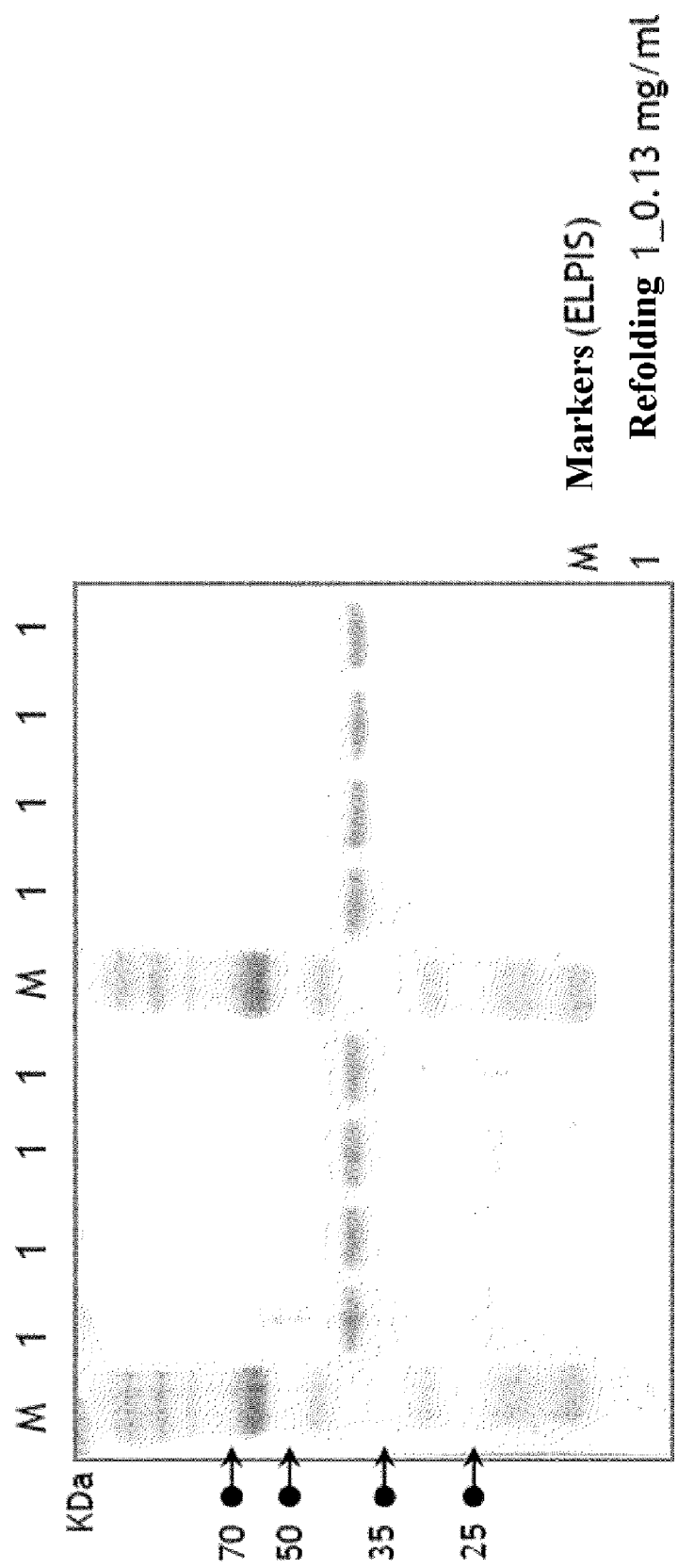
FIG. 2 illustrates the purification results for the constructed proteins for detecting bacteria.

Experimental Example 1. Identification of Expression of Protein for Detecting Bacteria After a 12% acylamide gel was made to 1 mm thickness, 20 µl (0.13 mg/ml) of the recombinant protein expressed in Example 1 was loaded on the gel and then run for 1.5 hours at 120 V. This was stained with Coomassie brilliant blue. The expression of protein was identified using markers for identifying molecular weight, and the results are illustrated in FIG. 2. As illustrated in FIG. 2, the purified recombinant protein of about 40 kDa in size for detecting bacteria was identified.

Experimental Example 2. Identification of Probe for Detecting Bacteria

In order to develop a probe for detecting bacteria under optimized conditions, attempts were made to seek an optimized ratio of quenching molecules (Quencher-NAA or Quencher-NAG) at which fluorescence signals of the fluorescent protein (TAMRA-PG or TAMRA-GP) prepared in the step of Example 2 are reduced. The combined groups having the respective ratios were mixed for 14 hours. Then, the results obtained by measuring fluorescence signals (ex: 547 nm, em: 576 nm) are illustrated in FIG. 3.

Figure 3:
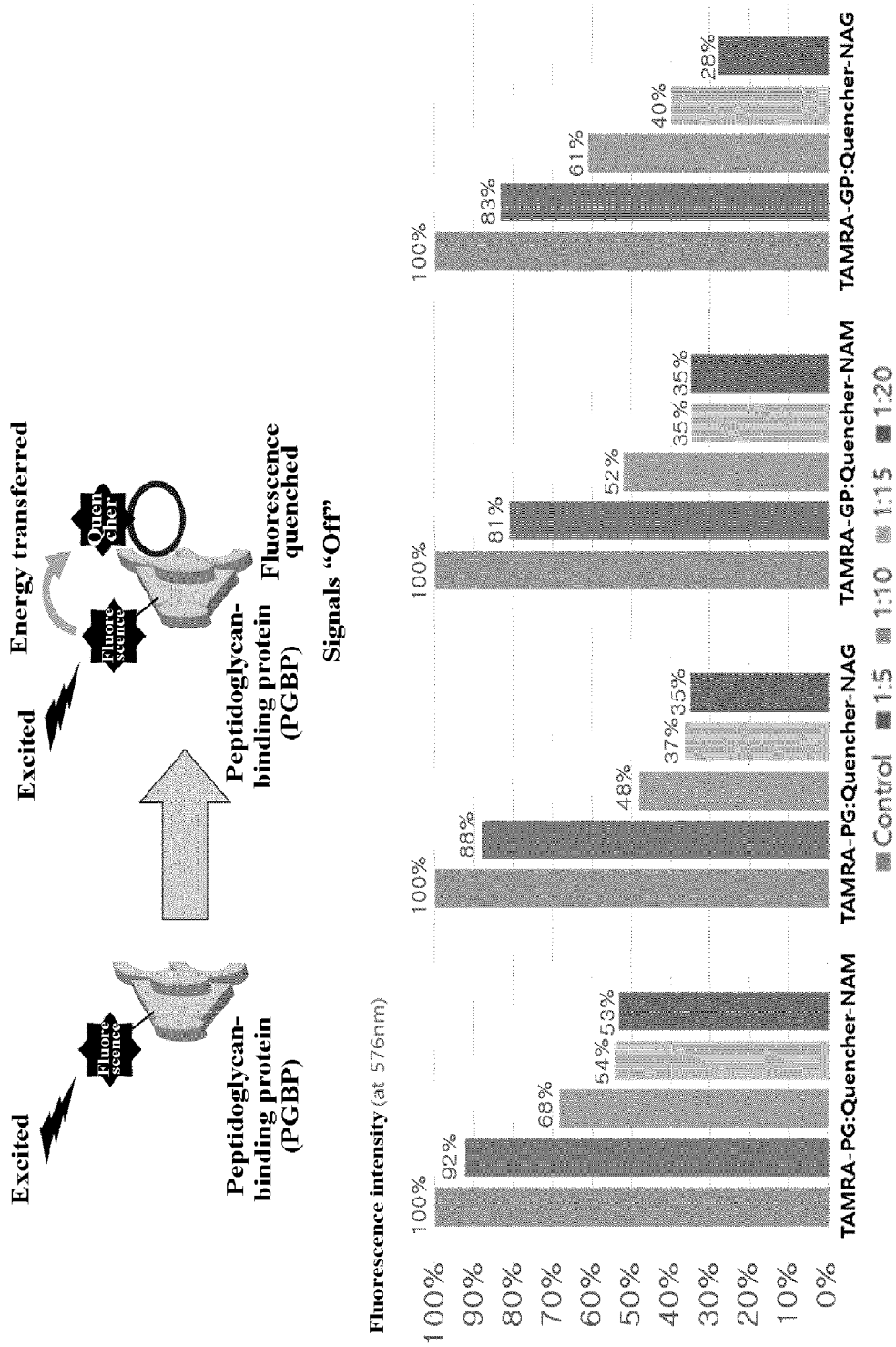
FIG. 3 illustrates a view of identifying fluorescence development by treating a peptidoglycan-containing sample with the probe according to the present invention.

As illustrated in FIG. 3, it has been found that fluorescence signals are decreased as the ratio of quenching molecules increases.

Experimental Example 3. Analysis on Detection Ability of Probe for Detecting Bacteria 3-1. Identification of Specific Detection for Bacteria In order to identify the detection specificity achieved through the probe for detecting bacteria according to the present invention, the following experiments were conducted using the probe prepared in Example 2.

A yeast species *S. cerevisiae* (*Saccharomyces cerevisiae*) and bacteria *S. aureus* were cultured, and the CFU count of each bacteria was determined by measuring an O.D. value at 600 nm. Each bacteria was loaded in a 96-well plate in an amount of 100 µl at a concentration of $10^6$-$10^1$ CFU/well, and then was treated with the probe. The concentration of the probe used for treatment was 5 µg on a protein basis. The mixture of probe and bacteria was reacted for 1 hour while shaking, and then measured using the absorption wavelength at 547 nm and the fluorescent wavelength at 576 nm in accordance with the fluorescence properties of TAMRA. The results are illustrated in FIG. 4.

Figure 4:
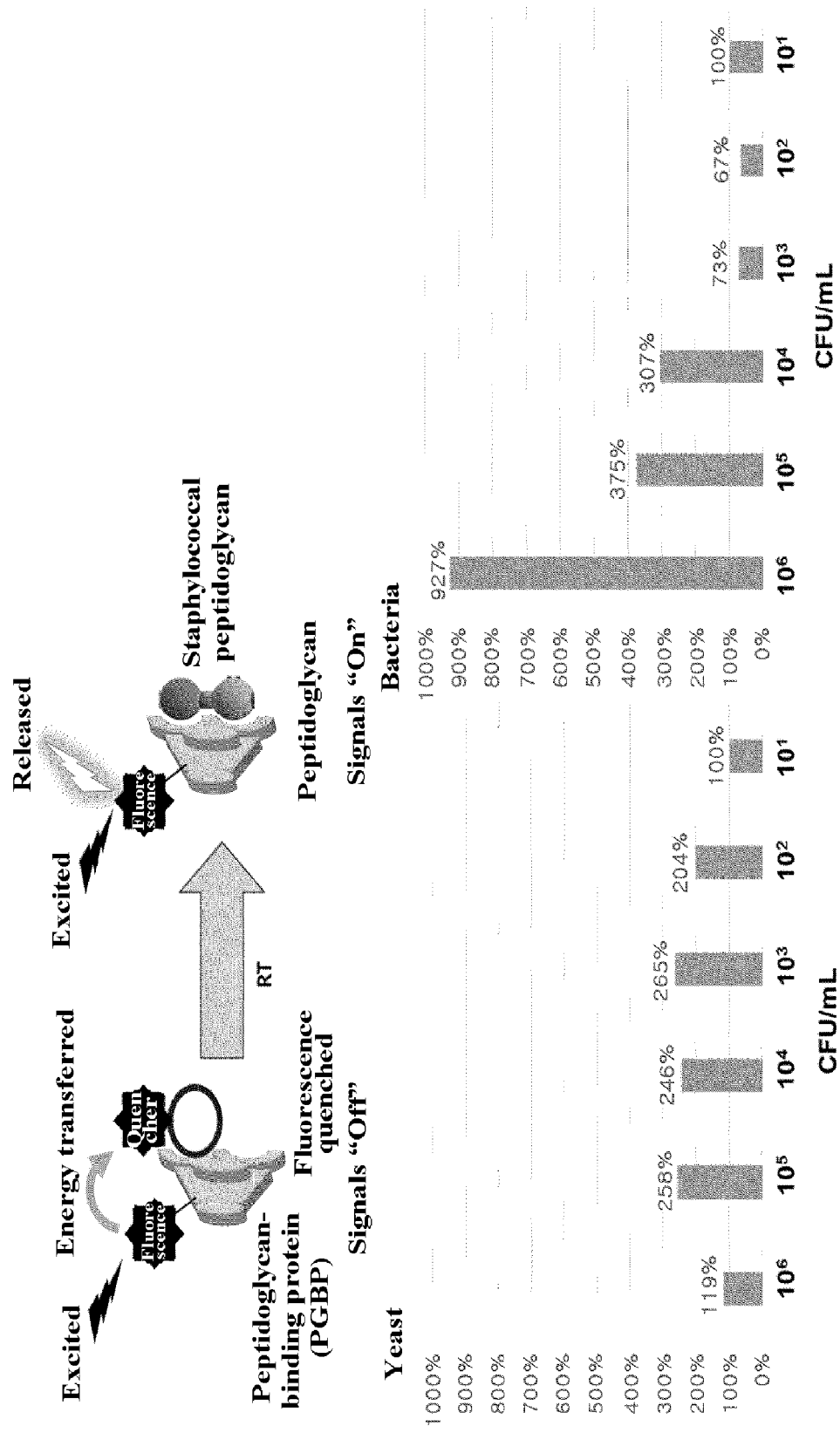
FIG. 4 illustrates a view of identifying whether the probe according to the present invention specifically detects bacteria.

As illustrated in FIG. 4, *S. cerevisiae* was a yeast species and lacked a peptidoglycan layer, and thus fluorescence intensity was not detectable. In *S. Aureus*, it has been found that fluorescence intensity was greatly increased by the probe of the present invention. In addition, the effect of detection was identifiable even at a minimum of $10^4$ CFU/well. This indicates that the detection of bacteria can be effectively identified through the probe of the present invention.

3-2. Measurement of Fluorescence Intensity by the Volumetric Ratio of Quencher

In order to identify the characteristics of the probe for detecting bacteria according to the present invention, bacteria *S. Aureus* was cultured together with the probe prepared in the step of Example 2. The O.D. value was measured at 600 nm to prepare $10^5$ CFU/ml of bacteria. The bacteria was loaded into a 96-well plate in an amount of 100 µl, and treated with the same concentration of probe as in Experimental Example 2. Measurement was performed every 1.5 minutes (90 seconds) for about 30 minutes using the absorption wavelength at 547 nm and the fluorescent wavelength at 576 nm in accordance with the fluorescence properties of TAMRA. The results are illustrated in FIG. 5.

Figure 5:
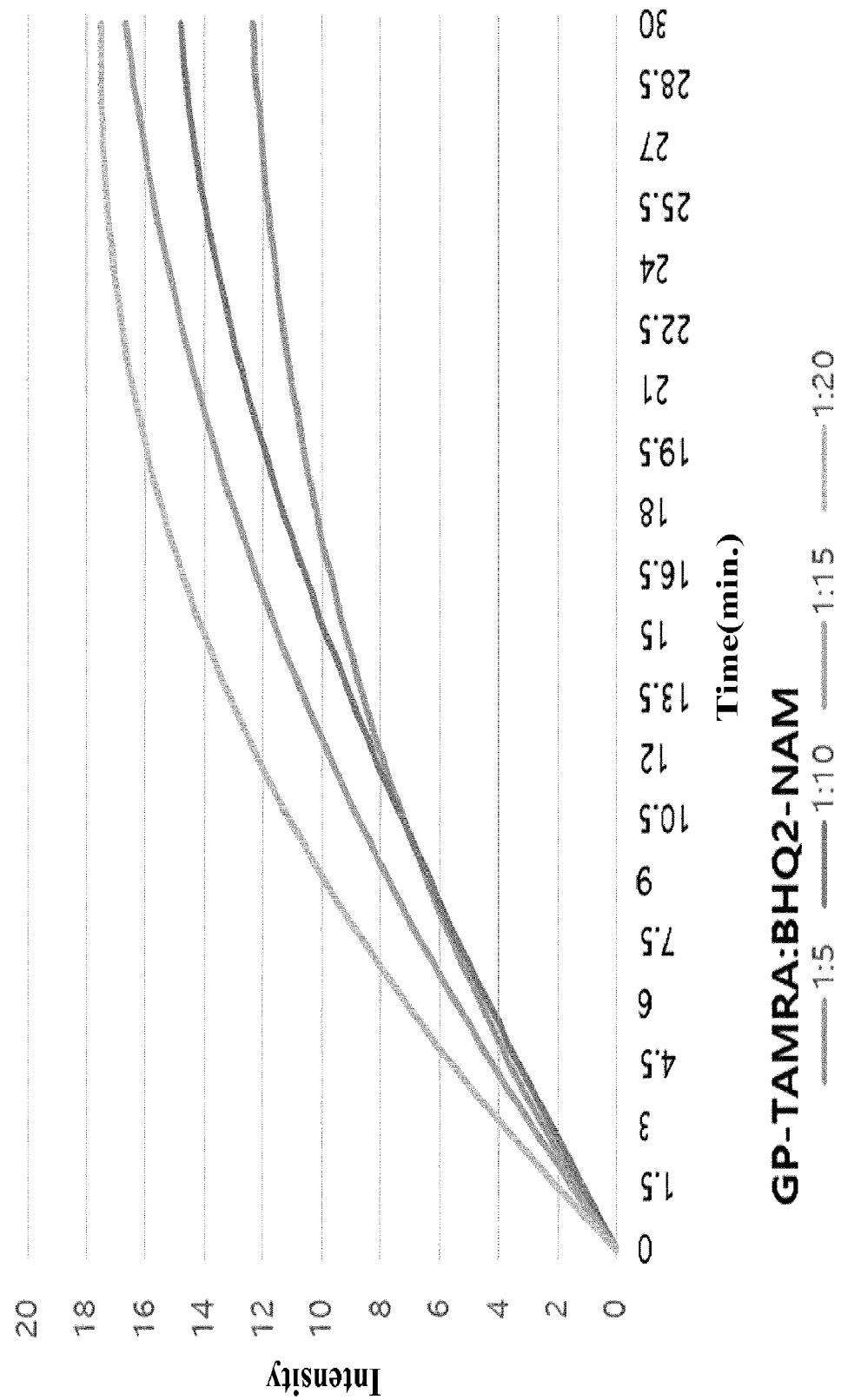
FIG. 5 illustrates a view of identifying that fluorescence signals before and after treatment with a peptidoglycan are increased as the volumetric ratio of the quencher in the probe increases.
Figure 6:
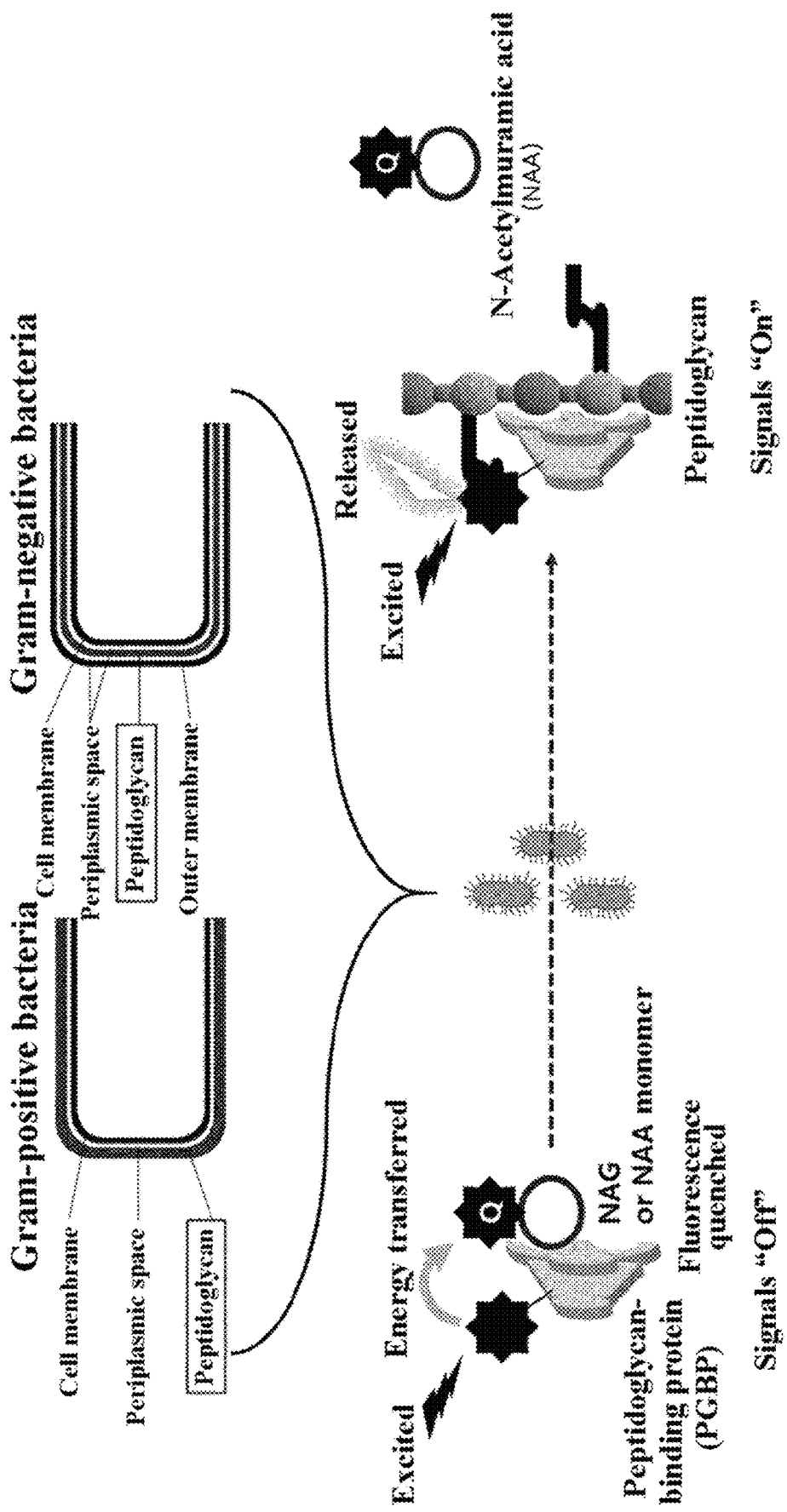
FIG. 6 illustrates the location of a peptidoglycan layer in bacteria and the way of operation for the probe according to the present invention.

As illustrated in FIG. 5, it has been found that 1) fluorescence signals are increased as the detection time increases and 2) fluorescence signals before and after treatment with a peptidoglycan are increased as the volumetric ratio of the quencher in the probe prepared in the step of Example 2 increases.

What is claimed is:

1. A probe for detecting bacteria, the probe comprising a peptidoglycan-binding protein (PGBP), a fluorescent material, and a quencher wherein the peptidoglycan-binding protein consists of the amino acid sequence of SEQ ID NO: 2 or SEQ ID NO: 3;
   wherein the quencher is linked to the peptidoglycan-binding protein through N-acetylmuramic acid (NAA) or N-acetyl-D-glucosamine (NAG) which is bound to the quencher.

2. The probe according to claim 1, wherein the fluorescent material is a luminous molecule, a metal ion, an organic dye, a conductor, a semiconductor, an insulator, a quantum dot, or a quantum wire.

3. The probe according to claim 1, wherein the quencher is any one or more selected from the group consisting of Black Hole Quencher-1 (BHQ-1), 4-(dimethylaminoazo) benzene-4-carboxylic acid (DABCYL), Eclipse, N,N,N',N'-tetramethyl-6-carboxyrhodamine (TAMRA), QSY-7, Black Hole Quencher-2 (BHQ-2), and Black Hole Quencher-3 (BHQ-3).

4. The probe according to claim 1, wherein a mixing ratio of the peptidoglycan-binding protein to the quencher is 1:1 to 40 (v/v).

5. A method for preparing a probe for detecting bacteria, the method comprising:
   a) binding a fluorescent molecule to a peptidoglycan-binding protein that consists of the amino acid sequence of SEQ ID NO: 2 or SEQ ID NO: 3;
   b) preparing a quencher to which N-acetylmuramic acid or N-acetyl-D-glucosamine is bound; and
   c) binding the fluorescent molecule-bound peptidoglycan-binding protein in a), with the quencher to which N-acetylmuramic acid or N-acetyl-D-glucosamine is bound in b).

6. A method for detecting bacteria, the method comprising treating a sample with the probe of claim 1.

7. The method according to claim 6, wherein the probe binds to a peptidoglycan of bacteria, thereby generating fluorescence.

* * * * *